United States Patent [19]

Stephenson

[11] Patent Number: 5,392,847
[45] Date of Patent: Feb. 28, 1995

[54] THERMAL MEDICAL BLANKET USING INTERNAL SUBTUBE

[75] Inventor: James G. Stephenson, Marshall, Mich.

[73] Assignee: Progressive Dynamics, Inc., Marshall, Mich.

[21] Appl. No.: 158,572

[22] Filed: Nov. 29, 1993

[51] Int. Cl.6 .......................... A47C 27/08; A61F 7/00
[52] U.S. Cl. ............................ 165/46; 62/261; 607/104; 607/107
[58] Field of Search .............. 165/46, 170; 62/259.3, 62/261; 5/423; 607/104, 107, 108; 137/561 A

[56] References Cited

U.S. PATENT DOCUMENTS

| | | | |
|---|---|---|---|
| 1,777,982 | 10/1930 | Popp | 4/535 |
| 2,093,834 | 9/1937 | Gaugler | 607/107 X |
| 2,532,918 | 12/1950 | Hungerford, Jr. | 137/561 A |
| 2,601,189 | 6/1952 | Wales, Jr. | 4/160 |
| 4,572,188 | 2/1986 | Augustine et al. | 607/107 |
| 4,660,388 | 4/1987 | Greene, Jr. | 62/261 |
| 4,777,802 | 10/1988 | Feher | 62/3 |
| 4,809,744 | 3/1989 | Bhat | 137/561 A |
| 4,867,230 | 9/1989 | Voss | 165/46 |
| 5,044,364 | 9/1991 | Crowther | 607/107 |
| 5,095,930 | 3/1992 | Stroszynski et al. | 137/561 A X |
| 5,125,238 | 6/1992 | Ragan et al. | 62/259.3 |
| 5,165,400 | 11/1992 | Berke | 128/400 |
| 5,184,612 | 2/1993 | Augustine | 607/104 |
| 5,246,656 | 9/1993 | Stephenson et al. | 264/153 |
| 5,265,599 | 11/1993 | Stephenson et al. | 607/104 |

FOREIGN PATENT DOCUMENTS 3106822 10/1982 Germany ................ 137/561 A

Primary Examiner—John Rivell
Assistant Examiner—L. R. Leo
Attorney, Agent, or Firm—Beaman & Beaman

[57] ABSTRACT

A pneumatic, disposable, temperature control blanket pressurized with a heated or cooled air comprises an inflated envelope having a lower sheet having openings formed therein for impinging the air upon a patient. Air is introduced into the blanket envelope at a single inlet port, and an interior flexible conduit or subtube located within the envelope communicates with the inlet for distributing freshly introduced air throughout the blanket length with little temperature loss.

5 Claims, 1 Drawing Sheet

THERMAL MEDICAL BLANKET USING INTERNAL SUBTUBE

BACKGROUND OF THE INVENTION

1. Field of the Invention

The invention pertains to medical body temperature control blankets of the pneumatic disposable type wherein an envelope defined by synthetic plastic sheets is pressurized by a temperature regulated air and the air is ejected upon the patient through the blanket lower sheet.

2. Description of the Related Art

A common treatment for post-surgery trauma, hypothermia and other life threatening temperature related trauma is to place a body temperature control blanket over the patient and impinge air upon the patient's body at a desired temperature to endeavor to raise, or lower, the temperature of the body. Usually, the patient is treated with heated air, but it is also possible to use blankets of this type to distribute cool air over the patient. Such thermal blankets take a variety of forms, and a lightweight disposable version of the general type of the instant invention is shown in the assignee's U.S. Pat. Nos. 5,125,238 and 5,246,656, and the purpose and advantages of this type of blanket are set forth in these patents.

A disposable temperature controlling blanket is usually formed of synthetic thermoplastic sheets, such as of a vinyl material which are heat sealed at their periphery to define a blanket. Openings located within the lower sheet permit the pressurized air within the blanket as supplied through an inlet port to be distributed over the patient's body. Usually, the upper and lower sheets will be welded or tacked at spaced locations to control the extent of envelope inflation, as will be appreciated from the disclosure of U.S. Pat. No. 5,125,238.

For a variety of reasons, it is desirable to locate the blanket pressurized air inlet port at the blanket lower end, with respect to the patient's head, and accordingly, heated air introduced into the blanket lower end tends to cool as the air travels the length of the blanket due to the fact that the blanket sheets are directly exposed to the ambient air. Such cooling of the temperature control air introduced into the blanket envelope prevents an even temperature of air from being distributed over the patient's entire body, and the even distribution of air temperature within the blanket envelope is a serious problem.

Patents for improving the distribution of substantially equal temperature air throughout the blanket is shown in the assignee's U.S. Pat. No. 5,265,599 entitled Patient Temperature Control Blanket With Controlled Air Distribution, and Ser. No. 08/078,842, now U.S. Pat. No. 5,304,217. In these disclosures, an enlarged air passage is defined within the central region of the envelope in communication with the pressurized air inlet as defined by closely spaced weldments or tacking wherein the upper and lower envelope sheets are heat sealed together. The forming of such a central air flow passage encourages the air entering the central region of the envelope to travel the length of the envelope before being laterally disbursed into the other blanket regions. This approach to achieving a more uniform distribution of the air temperature within the blanket envelope is generally successful, but because the upper and lower envelope sheets are exposed to ambient air, heat loss still occurs from the blanket central region as the air therein travels lengthwise through the blanket.

OBJECTS OF THE INVENTION

It is an object of the invention to provide a pneumatic disposable temperature control blanket having an interior air distribution conduit which permits a substantially uniform temperature of air to be distributed throughout the blanket length.

Another object of the invention is to provide a pneumatic disposable temperature control blanket having an interior conduit for receiving pressurized air which is inexpensive, which does not adversely affect the flexibility and foldability of the blanket, and which adds little cost to the blanket manufacture.

A further object of the invention is to provide a pneumatic disposable temperature control blanket employing an interior flexible air flow conduit wherein the transverse cross sectional area of the conduit is significantly less than the transverse cross sectional area of the blanket envelope whereby a space exists within the envelope surrounding the conduit insulating the conduit and reducing heat loss through the conduit.

SUMMARY OF THE INVENTION

A pneumatic disposable temperature control blanket in accord with the invention basically consists of upper and lower thermoplastic vinyl sheets sealed at their periphery, and tacked together intermediate their periphery at spaced locations to control inflation. The lower sheet includes a plurality of openings permitting the air within the blanket to impinge upon a patient located below the blanket, and an inlet air port defined in the blanket supplies the blanket interior with the temperature controlled air.

In the practice of the invention, a flexible subtube or conduit is located within the interior of the envelope having one end communicating with the inlet fitting, and the length of the conduit is disposed lengthwise of the blanket length, and preferably, the conduit is located within the central region of the blanket.

The transverse cross sectional area of the conduit is significantly less than the transverse cross sectional area of the blanket envelope central region in which it is located whereby a space exists between the inflated conduit and the inflated blanket. Orifices defined along the length of the conduit permit the air within the conduit as received from the inlet port to flow into the envelope, and hence, into the envelope lateral regions and through the lower sheet openings upon the patient.

Because the internal conduit is surrounded by a space within the envelope filled with temperature regulated air, usually heated air, the temperature differential between the air within the conduit and the air surrounding the conduit is small, reducing the heat loss within the air in the conduit. In this manner, by regulating the spacing and size of the orifices within the conduit, it is possible to insure that the temperature of the air being released into the envelope throughout its length is substantially constant permitting a substantially uniform air temperature throughout the blanket as ejected upon the patient.

The flexible nature of the subtube or conduit, as formed of vinyl, does not interfere with the folding of the blanket for packaging or storage purposes, and the inexpensive construction of the conduit adds little cost to the assembly.

BRIEF DESCRIPTION OF THE DRAWINGS

The aforementioned objects and advantages of the invention will be appreciated from the following description and accompanying drawings wherein.

DESCRIPTION OF THE PREFERRED EMBODIMENT

Figure 1:
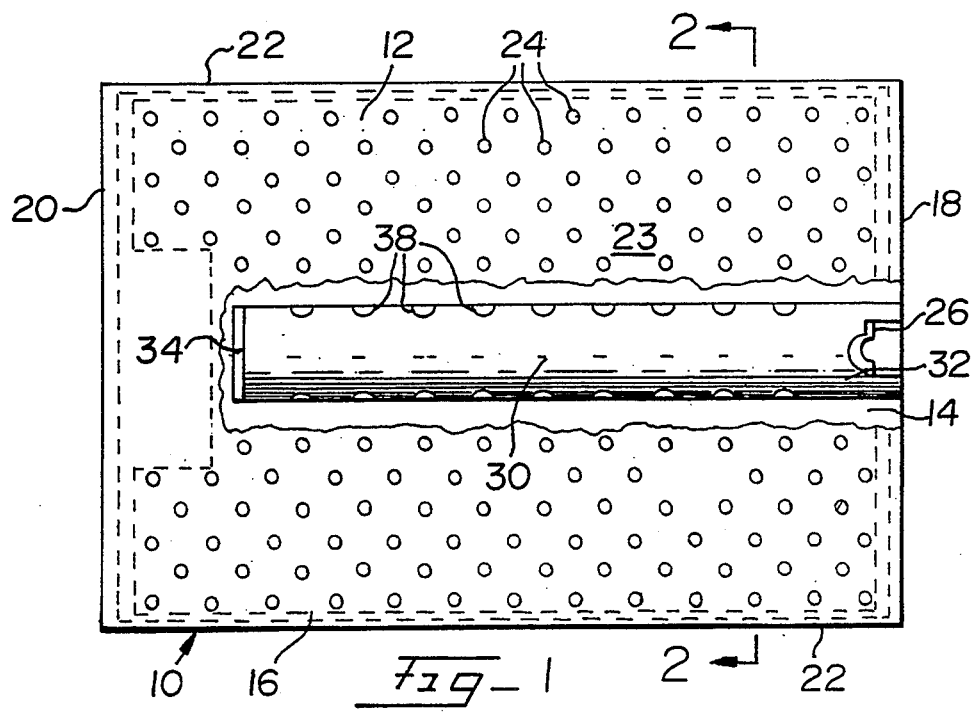
FIG. 1 is a top plan view of a pneumatic disposable temperature control blanket in accord with the invention, the central region thereof being broken away to illustrate the subtube or conduit located therein.

A disposable pneumatic temperature control blanket in accord with the invention basically consists of an envelope 10 defined by an upper sheet 12 and a lower sheet 14 of thermoplastic vinyl. The sheets, in their usual form, are of a generally rectangular configuration.

The envelope 10 includes a periphery 16 wherein the sheets are heat sealed together to define an air tight assembly, and the foot end of the envelope 10 is represented at 18, while the head end is designated by reference numeral 20. The envelope includes parallel lateral edges 22 and a central region 23 is defined between the edges 22. In order to control the inflation of the envelope 10, a plurality of spaced welds or tacks 24 interconnect the sheets 12 and 14.

Pressurized temperature control air is introduced into the envelope 10 at a folding inlet fitting 26, whereby the air supply nozzle, not shown, is received by the inlet fitting 26. The air within the envelope 10 escapes the envelope through the openings 28 defined in the lower sheet 14.

The aforedescribed blanket structure is identical to that shown in the assignee's U.S. Pat. No. 5,125,238, and this patent and the disclosure therein is herein incorporated by reference as to details of manufacture and operation.

Figure 2:
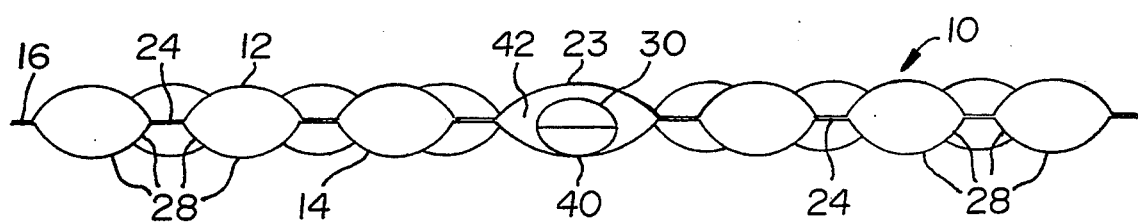
FIG. 2 is an elevational sectional view taken through Section 2—2 of FIG. 1, illustrating the blanket in an inflated condition.

A subtube or conduit 30 is located within the envelope 10 at the central region 23 as will be appreciated from FIGS. 1 and 2. The conduit 30 is preferably formed of a flexible vinyl material similar to that forming the sheets 12 and 14, and will form a generally cylindrical configuration when inflated as will be appreciated from FIG. 3. The conduit 30 includes an end 32 directly connected to the inlet port fitting 26 whereby all of the air injected into the inlet fitting 26 will be directly received within the conduit 30. The opposite end 34 of the conduit is usually closed, but small orifices may be defined therein if desired.

Figure 3:
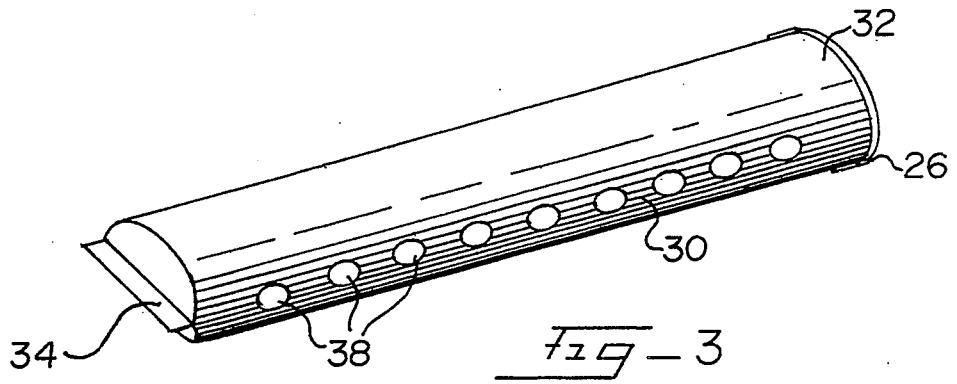
FIG. 3 is a perspective view of the subtube or conduit, per se, when inflated.

A plurality of ports or orifices are defined along the length of the conduit 30 as will be appreciated from FIGS. 1 and 3. Lateral orifices 38 are defined upon opposite sides of the conduit 30 opening to interstitial space between sheets 12 and 14. The lateral openings 38 closest to the closed end 34 of central conduit 30 may be larger in diameter than the other orifices 38.

Preferably, the conduit 30 is not attached or welded to either of the sheets 12 or 14, and it will be appreciated that the envelope central region 23 does not include tacks 24 in order to permit the reception of the conduit 30 within the envelope 10. As will be appreciated from FIG. 2, the transverse cross sectional area of the conduit 30, when inflated, is substantially less than the transverse cross sectional area of the envelope 10 in the central region 23, and the only location of touching of the conduit 30 with the sheets defining the envelope 10 will be at 40 wherein the lower portion of the conduit will be touching the lower sheet 14. Preferably, the conduit 30 is not attached to the envelope 10, although it may be desirable to tack the portion of the conduit 30 adjacent lower sheet 14 to lower sheet 14 adjacent end 34 to assure proper orientation of the conduit 30 within the envelope.

The fact that the transverse cross sectional area of the inflated conduit 30 is significantly less than that of the envelope central region 23 will permit a significant space 42 to substantially surround the periphery of the inflated conduit 30, and the space 42 serves to "insulate" the conduit 30 from the ambient air surrounding the envelope 10. As the air entering the inlet 26 is directly received by the conduit 30, the pressurized air within the conduit 30 flows through the orifices 38 into the lateral regions of the envelope 10. The air within the space 42 surrounding the conduit 30 will only be of a slightly lower temperature than the air within the conduit 30, and thus the presence of the space 42 will prevent significant temperature loss through the walls of the conduit as the air traverses the length of the conduit. Accordingly, the air leaving the conduit 30 through the orifices 38, regardless of the location of the orifices relative to the inlet fitting 26, will substantially be the same, insuring that the temperature of the air being distributed throughout the envelope area is substantially the same permitting an even air temperature flow upon the patient.

Because the conduit 30 is formed of a flexible vinyl the conduit does not interfere with the folding of the envelope 10 which occurs when the blanket is packaged, and the low cost of the conduit 30 adds little to the total cost of the blanket assembly.

It is appreciated that various modifications to the inventive concepts may be apparent to those skilled in the art without departing from the spirit and scope of the invention.

I claim:

1. In a pneumatic, disposable, temperature control blanket receiving conditioned air through an external air supply connection wherein the blanket comprises an upper elongated flexible sheet and a lower elongated flexible sheet, the sheets being sealed together at their peripheries to define an elongated envelope having a length defined by first and second ends, and having lateral edges and a central region intermediate the lateral edges, a plurality of air flow openings defined within the lower sheet, and an inlet air port defined in the envelope for supplying pressurized air to the envelope, the improvement comprising a plurality of spaced fasteners interconnecting the upper and lower sheets intermediate the envelope ends and lateral edges, an elongated flexible conduit within the envelope of lesser transverse cross sectional area than the envelope disposed lengthwise to the envelope length intermediate said fasteners and in communication with the inlet air port, said conduit having lateral sides, and a plurality of air orifices defined only in said conduit lateral sides along its length whereby air received within said conduit is distributed along the length of the interior of the envelope, said conduit being of lesser transverse cross sectional area than the envelope when pressurized whereby a space exists between the majority of the circumference of said conduit and the envelope upon said conduit and envelope being pressurized whereby said conduit will be substantially surrounded by air of the temperature within the envelope.

2. In a pneumatic, disposable, temperature control blanket as in claim 1, said conduit having first and second ends, said first end being connected to the inlet air port.

3. In a pneumatic, disposable, temperature control blanket as in claim 2, said second conduit end being closed.

4. In a pneumatic, disposable, temperature control blanket as in claim 2, the inlet air port being defined in the first end of the envelope and said conduit first end being disposed adjacent the envelope first end.

5. In a pneumatic, disposable, temperature control blanket as in claim 4, the inlet air port being located in the envelope first end substantially equidistant from the envelope lateral edges and said conduit being located within the envelope central region.

* * * * *